(12) United States Patent  (10) Patent No.: US 7,917,401 B2
Baker  (45) Date of Patent: Mar. 29, 2011

(54) SYSTEMS AND METHODS FOR OBTAINING HEALTH AND FINANCIAL INFORMATION WITH A HANDHELD DEVICE

(76) Inventor: Trent Baker, Salt Lake City, UT (US)

(*) Notice: Subject to any disclaimer, the term of this patent is extended or adjusted under 35 U.S.C. 154(b) by 978 days.

(21) Appl. No.: 11/277,994

(22) Filed: Mar. 30, 2006

(65) Prior Publication Data

US 2007/0088746 A1  Apr. 19, 2007

Related U.S. Application Data

(60) Provisional application No. 60/667,933, filed on Apr. 4, 2005.

(51) Int. Cl.
*G06Q 30/00* (2006.01)
(52) U.S. Cl. ........ 705/26.1; 705/27.1; 705/30; 715/744; 715/766; 186/61
(58) Field of Classification Search .................... 705/26, 705/27, 26.1, 27.1, 30; 715/744, 766; 186/61
See application file for complete search history.

(56) References Cited

U.S. PATENT DOCUMENTS

| | | | |
|---|---|---|---|
| 5,789,732 A | 8/1998 | McMahon | |
| 6,134,548 A | 10/2000 | Gottsman | |
| 6,317,718 B1 | 11/2001 | Fano | |
| 6,587,835 B1 | 7/2003 | Treyz | |
| 6,837,436 B2 | 1/2005 | Swartz | |
| 6,859,212 B2* | 2/2005 | Kumar et al. | 715/744 |
| 6,873,967 B1 | 3/2005 | Kalagnanam | |
| 2002/0002504 A1* | 1/2002 | Engel et al. | 705/26 |
| 2002/0139617 A1* | 10/2002 | Goodwin, III | 186/61 |
| 2003/0043195 A1* | 3/2003 | Kling et al. | 345/766 |
| 2005/0274792 A1* | 12/2005 | Hahn-Carlson et al. | 235/379 |

* cited by examiner

*Primary Examiner* — Yogesh C Garg
(74) *Attorney, Agent, or Firm* — Trent H. Baker; Baker & Associates PLLC

(57) ABSTRACT

The present invention relates to systems and methods for obtaining financial information with a handheld device. One embodiment of the present invention relates to a system for obtaining real time financial information utilizing a bar code or RF ID reader on a handheld device. A bar code or RF ID reader is used to obtain the product identity of a particular product in a retail environment. The product identity is correlated with the particular retailer's product price. This information can then be analyzed versus current financial budgets or recorded as part of a financial plan. In addition, real time financial advice and information can be given on the product including whether a competitor offers a lower price on a similar product, consumer reviews of the product, value rating, etc. The bar code or RF ID reader may be incorporated into any existing handheld device including a PDA, media player, cell phone, calculator, watch, or shopping device.

10 Claims, 4 Drawing Sheets

SYSTEMS AND METHODS FOR OBTAINING HEALTH AND FINANCIAL INFORMATION WITH A HANDHELD DEVICE

RELATED APPLICATIONS

This application claims priority to U.S. provisional application Ser. No. 60/667,933 filed Apr. 4, 2005.

BACKGROUND

1. Field of the Invention

The present invention relates to systems and methods for obtaining health and financial information with a handheld device. More particularly, the present invention relates to utilizing a bar-code reader or RF ID reader on a handheld device to obtain real time health and financial information.

2. Background of the Invention and Related Art

Two of the major problems faced by individuals in industrialized nations are related to finances and health concerns. It is estimated that a large percentage of the industrialized population spends more money than they make and is medically considered extremely unhealthy. In order to overcome these problems, people conventionally create budgets and goals for both financial and health items. These budgets include how much money they are going to spend and the types of food they are going to consume. Unfortunately, very few individuals or families continue using budgets over long periods of time because they require extensive time to create and maintain.

A financial budget is conventionally created by recording all purchases in a log or a computer program. This information is then compared with income and a budget is created that enables sufficient spending without exceeding income amount. All spending must be manually entered in order to assess whether a budget is being achieved or if it is being exceeded. Even if a credit card is used for all purchases, the credit card statement does not correlate purchases into categories that are useful in a financial planning. Because of the excess time involved in recording purchases, many individuals simply estimate and often fail to adhere to their budgets.

Likewise, many people are beginning to create health budgets in which they determine optimum nutritional levels in which to consume. The nutritional levels include calories, fat, sugar, carbohydrates, protein, etc. In order to assess whether the health budget is maintained, an individual must manually enter all of the food they consume. Therefore, people eventually rarely maintain health budgets for long periods of time. There is also a strong psychological stigma that labels nutritional records as extreme measures that should only be practiced by severely unhealthy individuals.

Accordingly, there is a need in the industry for a system that enables financial and health information to be obtained and recorded in an efficient manner that facilitates easier financial and health budgeting.

SUMMARY OF THE INVENTION

The present invention relates to systems and methods for obtaining health and financial information with a handheld device. One embodiment of the present invention relates to a system for obtaining real time financial information utilizing a bar code reader on a handheld device. A bar code or RF ID reader is used to obtain the product identity of a particular product in a retail environment. The product identity is correlated with the particular retailer's product price. This information can then be analyzed versus current financial budgets or recorded as part of a financial plan. In addition, real time financial advice and information can be given on the product including whether a competitor offers a lower price on a similar product, consumer reviews of the product, value rating, etc. A second embodiment of the present invention relates to a system for providing real time health information utilizing a bar code or RF ID reader on a handheld device. The bar code or RF ID reader could be used to obtain a product identity in a retail or home environment. Health information is correlated with the product based on the product's identity. This information could then be used for a variety of health related purposes including ingredient alerts, high fat content, high calorie content, nutritional budgets, etc. Alternatively, products could be scanned before consumption in the home environment to assist in health budgets for particular nutritional values such as calories, fat, carbohydrate, or protein. The bar code or RF ID reader for both embodiments may be incorporated into any existing handheld device including a PDA, cell phone, calculator, watch, or shopping device.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
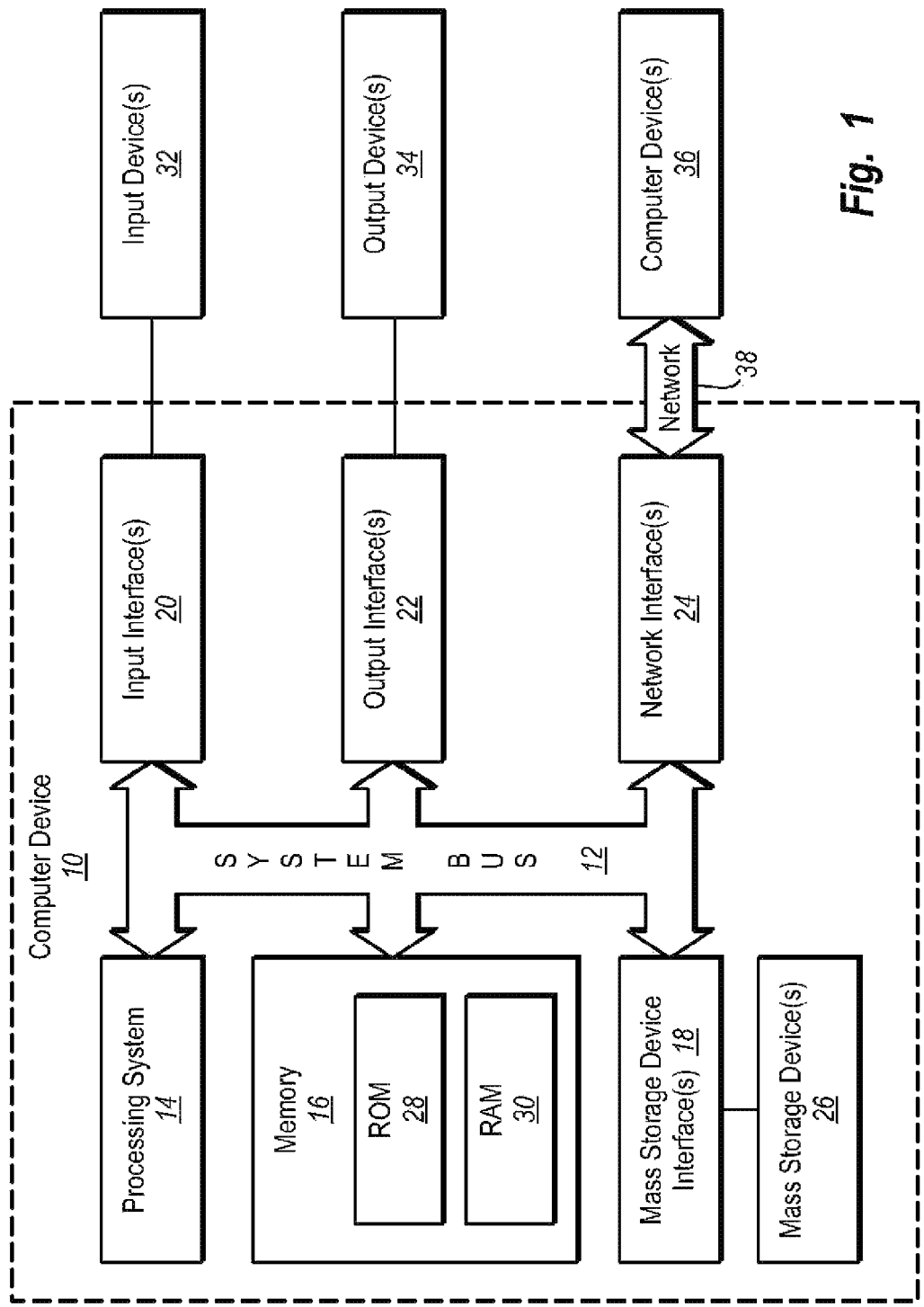
FIG. 1 illustrates a representative system that provides a suitable operating environment for use with the present invention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The present invention relates to systems and methods for obtaining health and financial information with a handheld device. One embodiment of the present invention relates to a system for obtaining real time financial information utilizing a bar code or RF ID reader on a handheld device. A bar code or RF ID reader is used to obtain the product identity of a particular product in a retail environment. The product identity is correlated with the particular retailer's product price. This information can then be analyzed versus current financial budgets or recorded as part of a financial plan. In addition, real time financial advice and information can be given on the product including whether a competitor offers a lower price on a similar product, consumer reviews of the product, value rating, etc. A second embodiment of the present invention relates to a system for providing real time health information utilizing a bar code or RF ID reader on a handheld device. The bar code or RF ID reader could be used to obtain a product identity in a retail or home environment. Health information is correlated with the product based on the product's identity. This information could then be used for a variety of health related purposes including ingredient alerts, high fat content, high calorie content, nutritional budgets, etc. Alternatively, products could be scanned before consumption in the home environment to assist in health budgets for particular nutritional values such as calories, fat, carbohydrate, or protein. The bar code or RF ID reader for both embodiments may be incorporated into any existing handheld device including a PDA, MEDIA PLAYER, cell phone, calculator, watch, or shopping device. While embodiments of the present invention are directed at systems and methods for obtaining health and financial information with a handheld device, it will be appreciated that the teachings of the present invention are applicable to other areas.

The following terms are defined accordingly for the purposes of this application:

"bar code"—is any digitally encoded product identity code including a UPC code, zero-compressed UPC code, a holographic code, RF code, etc. The bar code may be located directly on the product or on a product tag.

"handheld device"—any electrical device that can be held in the palm of a users hand including a cell phone, Ipod, media player, PDA, watch, mini computer, GPS unit, card, calculator, etc.

"bar code or RF ID reader"—any device that is capable of obtaining information from a product bar code or RF ID including a laser, an infrared (IR) port, a bar code scanner, a radio receiver, etc.

"nutritional value"—A quantity measurement of any nutritional value including calories, fat, carbohydrates, sugar, sodium, etc.

"product identity"—any information that can be used to obtain the identity of a product including a serial number, UPC code, product name, etc.

"financial record"—a record of financial transactions over a particular time period such as a month or a year.

"financial category"—any category of financial information including home, auto, food, beauty, work, travel, deductible, cost-basis, business expense, home repair, etc.

"corresponding health information"—any health information related to a product including all information contained on the mandatory FDA health label, ingredients, nutritional values, vegetarian related concerns, genetically modified origins, pesticide usage, animal treatment/testing, etc.

"a nutritional value budget"—any nutritional value amount summarized over a particular period, the nutritional value budget may be related to purchased nutritional values or consumed nutritional values; for example, a person may have a daily calorie budget of 2000 and a daily fat budget of 50 grams which are tabulated by the device and provided real time.

"a financial budget"—a financial amount over a particular time period; the financial budget may be related to purchased items or consumed items. The financial budget may also be directed at a particular category. For example, a $600 a month food budget.

The following disclosure of the present invention is grouped into two subheadings, namely "Exemplary Operating Environment" and "Financial/Health System". The utilization of the subheadings is for convenience of the reader only and is not to be construed as limiting in any sense.

Exemplary Operating Environment

FIG. 1 and the corresponding discussion are intended to provide a general description of a suitable operating environment in which the invention may be implemented. One skilled in the art will appreciate that the invention may be practiced by one or more computing devices and in a variety of system configurations, including in a networked configuration. Alternatively, the invention may also be practiced in whole or in part manually following the same procedures. Embodiments of the present invention embrace one or more computer readable media, wherein each medium may be configured to include or includes thereon data or computer executable instructions for manipulating data. The computer executable instructions include data structures, objects, programs, routines, or other program modules that may be accessed by a processing system, such as one associated with a general-purpose computer capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system.

With reference to FIG. 1, a representative system for implementing the invention includes computer device 10, which may be a general-purpose or special-purpose computer. For example, computer device 10 may be a personal computer, a notebook computer, a personal digital assistant ("PDA") or other hand-held device, a workstation, a minicomputer, a mainframe, a supercomputer, a multi-processor system, a network computer, a processor-based consumer electronic device, or the like.

Computer device 10 includes system bus 12, which may be configured to connect various components thereof and enables data to be exchanged between two or more components. System bus 12 may include one of a variety of bus structures including a memory bus or memory controller, a peripheral bus, or a local bus that uses any of a variety of bus architectures. Typical components connected by system bus 12 include processing system 14 and memory 16. Other components may include one or more mass storage device interfaces 18, input interfaces 20, output interfaces 22, and/or network interfaces 24, each of which will be discussed below. Processing system 14 includes one or more processors, such as a central processor and optionally one or more other processors designed to perform a particular function or task. It is typically processing system 14 that executes the instructions provided on computer readable media, such as on memory 16, a magnetic hard disk, a removable magnetic disk, a magnetic cassette, an optical disk, or from a communication connection, which may also be viewed as a computer readable medium.

Memory 16 includes one or more computer readable media that may be configured to include or includes thereon data or instructions for manipulating data, and may be accessed by processing system 14 through system bus 12. Memory 16 may include, for example, ROM 28, used to permanently store information, and/or RAM 30, used to temporarily store information. ROM 28 may include a basic input/output system ("BIOS") having one or more routines that are used to establish communication, such as during start-up of computer device 10. RAM 30 may include one or more program modules, such as one or more operating systems, application programs, and/or program data.

One or more mass storage device interfaces 18 may be used to connect one or more mass storage devices 26 to system bus 12. The mass storage devices 26 may be incorporated into or may be peripheral to computer device 10 and allow computer device 10 to retain large amounts of data. Optionally, one or more of the mass storage devices 26 may be removable from computer device 10. Examples of mass storage devices include hard disk drives, magnetic disk drives, tape drives and optical disk drives. A mass storage device 26 may read from and/or write to a magnetic hard disk, a removable magnetic disk, a magnetic cassette, an optical disk, or another computer readable medium. Mass storage devices 26 and their corresponding computer readable media provide nonvolatile storage of data and/or executable instructions that may include one or more program modules such as an operating system, one or more application programs, other program modules, or program data. Such executable instructions are examples of program code means for implementing steps for methods disclosed herein.

One or more input interfaces 20 may be employed to enable a user to enter data and/or instructions to computer device 10 through one or more corresponding input devices 32. Examples of such input devices include a keyboard and alternate input devices, such as a mouse, trackball, light pen, stylus, or other pointing device, a microphone, a joystick, a game pad, a satellite dish, a scanner, a camcorder, a digital camera, and the like. Similarly, examples of input interfaces 20 that may be used to connect the input devices 32 to the system bus 12 include a serial port, a parallel port, a game port, a universal serial bus ("USB"), a firewire (IEEE 1394), or another interface.

One or more output interfaces 22 may be employed to connect one or more corresponding output devices 34 to system bus 12. Examples of output devices include a monitor or display screen, a speaker, a printer, and the like. A particular output device 34 may be integrated with or peripheral to computer device 10. Examples of output interfaces include a video adapter, an audio adapter, a parallel port, and the like.

One or more network interfaces 24 enable computer device 10 to exchange information with one or more other local or remote computer devices, illustrated as computer devices 36, via a network 38 that may include hardwired and/or wireless links. Examples of network interfaces include a network adapter for connection to a local area network ("LAN") or a modem, wireless link, or other adapter for connection to a wide area network ("WAN"), such as the Internet. The network interface 24 may be incorporated with or peripheral to computer device 10. In a networked system, accessible program modules or portions thereof may be stored in a remote memory storage device. Furthermore, in a networked system computer device 10 may participate in a distributed computing environment, where functions or tasks are performed by a plurality of networked computer devices.

Financial/Health System

Figure 2:
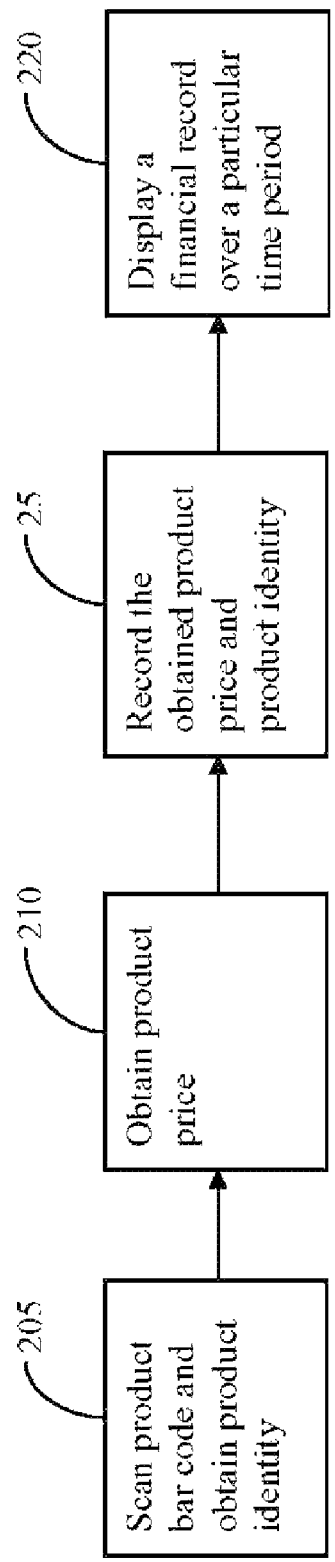
FIG. 2 illustrates a flow chart of one embodiment of a system for utilizing a bar code or RF ID reader on a handheld device to obtain and record financial information.

Reference is next made to FIG. 2, which illustrates a flow chart of one embodiment of a system for utilizing a bar code or RF ID reader on a handheld device to obtain and record financial information. The method is designated generally at 200. Initially, a bar code or RF ID is scanned such that product identity information is obtained, act 205. Various techniques and devices may be used for scanning the bar code or RF ID and obtaining the appropriate product identity. A handheld device equipped with a bar code or reader may be positioned near the bar code or such that the port can receive a particular data set based on the white and black regions of a conventional bar code. The received data will most likely contain a twelve digit number known as a Universal Product Code (UPC) code based on a particular UCC standard. The first six digits of a UPC code are the identification of the manufacturer, the next five digits are the product identification number, and the last digit is a check digit. Various other bar codes or UPC formats may be utilized including zero-compressed UPC codes and the like. The scanned code may be considered the product identity or may be further correlated with other information in a variety of ways to obtain more detailed product identity information. For example, a database of UPC codes may be stored on the handheld device such that it can determine the product name. Alternatively, the UPC code may be correlated with the product's name using a wireless data link such as the internet A product price for the scanned product is then obtained, act 210. The identity of the product can be correlated with a retailer's price list or network site to obtain the specific price. Various network procedures may be used to obtain the specific retailer's price including a conventional search, a worm, etc. It may also be necessary for the identity of the retailer to be automatically or manually obtained. Various automatic procedures for obtaining the identity of the retailer include using location/GPS information to obtain approximate address which can then be used to determine retailer identity by correlation with a network phone book. By performing a network search of both the retailer identity and the product identity, it may be possible to obtain the specific product price. Alternatively, the price could be scanned with a text recognition scanning device such as a low resolution digital camera coupled with text recognition software. And the price could easily be manually entered using a user input device. The various automatic price obtaining techniques may be sequentially performed before manually prompting the user for the price. The sequence of performing automatic and manual price obtaining techniques will end as soon as one of the techniques produces an accurate price. In addition, the user may manually enter the price if one of the automatic price techniques generates an incorrect price that is different from the displayed price identified by the user. Various other techniques may be used to obtain the product price and remain consistent with the present invention.

In addition, the product price and/or identity can be used to correlate with other information about the product which can be displayed to the user. For example, the product identity can be correlated with consumer reviews to obtain quality information which may affect whether the user wishes to purchase the product. Alternatively, the product price could be correlated with other price information such as other brands or the identical product at a different retailer. Pre-programmed alerts may also be displayed if it is determined that the product's price exceeds a financial budget or is pre-determined to be avoided.

The scanned product's price and identity are then recorded, act 215. The information is recorded on a data storage medium such as an optical hard disk or CD. The product identity and price may be used to assign the product to a particular financial category. For example, if the product identity is Campbell's tomato soup, the product could be assigned to a food category. This assigned category is also recorded with the product's price and identity for database management purposes. Additional variables and sub-categories may be created and assigned to the product for organization and correlation purposes. Additional products may be recorded from other data entry means. For example, credit card and bank account purchase information could be correlated with the recorded information to add purchases of items which the user did not scan. This allows a more complete record of all purchases to be recorded that includes scanned items and non-scanned items. Likewise, other products and corresponding information may be manually entered. In addition, the recorded information may interface with other financial software modules including Quicken and MS Money.

A financial record is then displayed that includes the recorded information about the products over a particular period of time, act 220. The financial record may be displayed on the device that scanned the product or a separate data linked device. The financial record may include displaying a monthly record of purchases including the most recent purchases. The financial record may also be subdivided into a particular category or variable for the purpose of determining a set of information. For example, the current deductible home repair purchases for the year of 2005. Various financial records incorporating the recorded product price and identity information can be displayed and remain consistent with the present invention.

Figure 3:
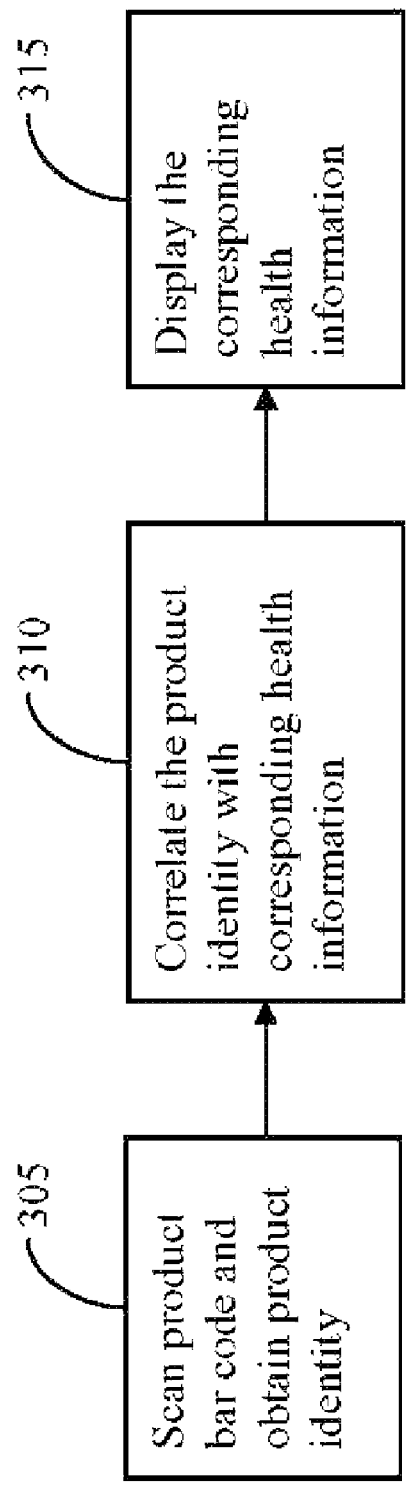
FIG. 3 illustrates a flow chart of one embodiment of a system for utilizing a bar code or RF ID reader on a handheld device obtain and record health information.

Reference is next made to FIG. 3, which illustrates a flow chart of one embodiment of a system for utilizing a bar code or RF ID reader on a handheld device to obtain and record health information. The method is designated generally at 300. Initially, a bar code or RF ID is scanned such that product identity information is obtained, act 305. Various techniques and devices may be used for scanning the bar code or RF ID and obtaining the appropriate product identity. A handheld device equipped with a bar code reader may be positioned near the bar code such that the port can receive a particular data set based on the white and black regions of a conventional bar code. The received data will most likely contain a twelve digit number known as a Universal Product Code (UPC) code based on a particular UCC standard. The first six digits of a UPC code are the identification of the manufacturer, the next five digits are the product identification number, and the last digit is a check digit. Various other bar codes or UPC formats may be utilized including zero-compressed UPC codes and the like. The scanned code may be considered the product identity or may be further correlated with other information in a variety of ways to obtain more detailed product identity information. For example, a database of UPC codes may be stored on the handheld device such that it can determine the product name. Alternatively, the UPC code may be correlated with the product's name using a wireless data link such as the internet.

The product's identity is then correlated with corresponding health information, act 310. The health information for a large number of products may be stored directly on the device which scans the product and/or the information may be obtained using some form of data link. For example, the conventional health information required on all product labels may be available from one source but other health information may be available elsewhere. Various identity correlation systems may be used individually or in conjunction to obtain the proper health information for the scanned product. Additional health information not included on many labels includes organic designations, genetically modified origins, corporate relations to undesired parent company, etc. Additional manually entered products may also be correlated with health information in the same manner.

The scanned product's identity and correlated information can also be recorded. The information is recorded on a data storage medium such as an optical hard disk or CD. The product identity and information may be used to assign the product to a particular health category. For example, if the product identity is Campbell's tomato soup, the product could be assigned to a soup or vegetable category. This assigned category is also recorded with the product's identity and correlated information for database management purposes. Additional variables and sub-categories may be created and assigned to the product for organization and correlation purposes. Additional products may be recorded from other data entry means. For example, credit card and bank account purchase information could be correlated with the recorded information to add purchases of items which the user did not scan. This allows a more complete record of all purchases to be recorded that includes scanned items and non-scanned items. Likewise, other products and corresponding information may be manually entered. In addition, the recorded information may interface with other health software modules.

In addition, various modules may be used to tabulate health budgets, alert to undesired ingredients, allergy information, etc utilizing the correlated health information. For example, an individual may scan products which they consume over a particular time period and the various nutritional values may be added for each of the items consumed to give an accurate total consumed nutritional value over a particular time period such as calories consumed or purchased in a week. An alert may be set to notify a user if an item is scanned for consumption that exceeds one or more tabulated threshold values. For example, if a user has already consumed 800 mg of sodium and then subsequently scans a can of V-8 for consumption, a notice could be displayed to alert the user they are exceeding their pre-programmed daily sodium value.

The correlated health information is displayed, act 315. The display of the correlated health information can be configured to only display desired nutritional values or tabulated total values. For example, a diabetic individual may wish to have the sugar content of every item displayed in addition to a tabulated daily sugar consumption value. The act of displaying the correlated health information may be performed on the device that scans the product or a separate device.

It should be noted that any of the acts described above may be performed manually or in some combination between a computer device and a manual operation. Likewise, multiple computer devices may be used to perform the acts and remain consistent with the present invention. The described methods may also be performed as a computer program product.

Figure 4:
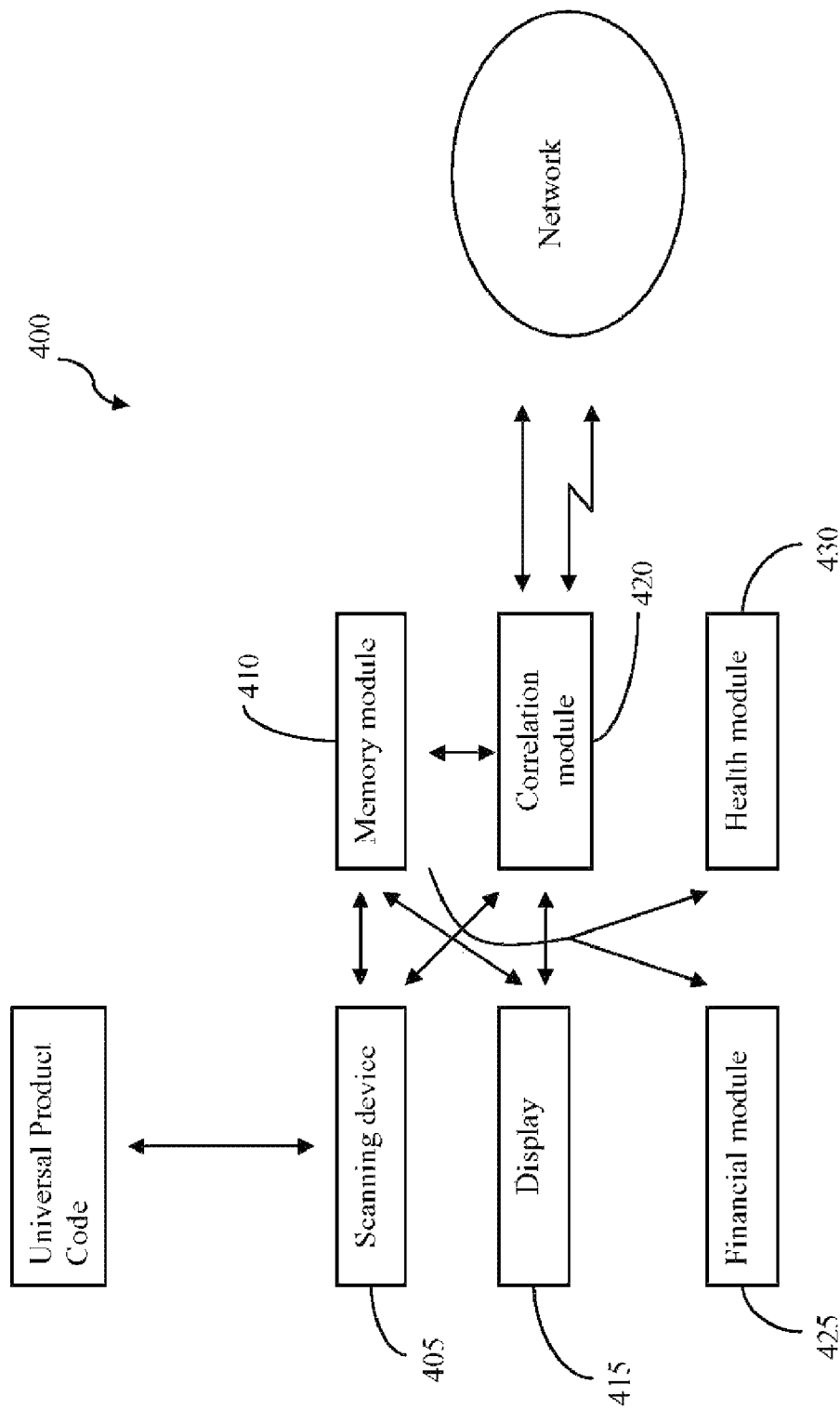
FIG. 4 illustrates a handheld system in accordance with one embodiment of the present invention.

Reference is next made to FIG. 4, which illustrates a handheld system in accordance with one embodiment of the present invention. The system is designated generally at 400. The system 400 generally includes a scanning device 405, a memory module 410, a display 415, a correlation module 420, a financial module 425, and a health module 430. The scanning device is capable of obtaining a product identity from a bar code. The product identity is the UPC 12 digit number or some other unique product identification embedded in the bar code. The scanning device may comprise an existing IR port or any other form of bar code reader. The device obtains the UPC code from a standard bar code which includes the manufacturer identity and the individual product code. The scanning device may also be configured to scan other forms digital data storage such as a holographic display or the like.

The memory module 410 is configured to store digital information. The memory module may comprise any data storage medium including a hard disk, tape drive, CD, DVD, etc. The illustrated embodiment of a memory module 410 interfaces with the other components in the manner shown. The memory module 410 may initially store the UPC code obtained by the scanning device for the scanned product. This stored UPC code can then be utilized by the correlation module 420.

The correlation module 420 is configured to correlate the scanned product with corresponding health or financial information. The correlation module 420 may compare the UPC code to a database stored on the memory module to obtain the corresponding health or financial information. Alternatively, the correlation module 420 may compare the UPC code to data located on an external network to obtain the health or financial information. The correlation module 420 may utilize a wired or wireless data communication system in order to communicate with the external network. The health information includes any health related information about the scanned product including nutritional information, ingredient information, product origin, potential chemicals usage in manufacturing the product, undesired parent company relation to manufacturer, consumer warnings, etc. The financial information includes any financial information about the scanned product including price, competitor price, other brand price, generic price, bulk price, price with tax, internet price, etc. The correlation module 420 may also be used to correlate non-scanned products with corresponding health or financial information. For example, a user may wish to purchase a street served hot dog with cash, this product may be manually entered and correlated with the appropriate information.

The display 415 is configured to visually display the information about the scanned product. The display 415 may be any form of visual display device including LCD, plasma, projection, etc. The display 415 can be configured to display information about the product in any format desired by a user.

The financial module 425 analyzes financial information obtained by the correlation module 420 and organizes the financial information in a manner to provide real time financial records. These records include financial budgets, thresholds, etc. For example, the financial module 425 may analyze a scanned product's price in relation to a monthly budget and produce a notification that the scanned product exceeds the monthly budget. Likewise, the financial module may analyze a scanned product's price and determine that a significant cost savings can be obtained by purchasing the same product online without tax from a particular website. The financial module 425 is also capable of producing various financial records including tax records, budget records, reporting records, etc. The financial module may include multiple modes of operation such as a preview mode, a purchase mode, a review mode, a business mode, etc. Each of these modes may correlate the financial information in a unique manner. For example, the preview mode may simply allow a user to preview the product price and obtain information before committing to purchase. The information obtained in preview mode may not be recorded permanently because the use may decide not to purchase the product. Likewise, the business mode may be used to assign all purchased items to a particular business for financial record keeping. In addition, the financial module can be configured to interface with an additional financial software module including Quicken or MS Money.

The health module 430 analyzes health information obtained by the correlation module 420 and organizes the health information in a manner to provide real time health records. These records include health budgets, thresholds, goals, etc. For example, the health module 430 may analyze the nutritional content in the scanned product (if it is food) and determine that it exceeds the user's daily fat grams for consumption. Likewise, the health module 430 may identify that the scanned product contains an ingredient which the user is allergic or wishes to avoid. The health module 430 is also capable of producing various health records including vitamin intake records, mineral intake records, nutritional intake records, calorie counts, etc. The health module may include multiple modes of operation such as a preview mode, a purchase mode, a consumption mode, a gift purchase mode, etc. Each of these modes may correlate the health information in a unique manner. For example, the preview mode may simply allow a user to preview the health information before purchasing or consuming the product. The information obtained in the preview mode may not be recorded permanently because the use may decide not to purchase or consume the product. In addition, the health module can be configured to interface with an existing health software module.

Alternatively, the present invention could be implemented to use with RF-ID rather than bar codes to obtain information. Naturally, the device would include a RF-ID reader in addition to or in place of the bar code scanner. The device could obtain similar identity information from the product using the RF-ID as the bar code scanner.

Thus, as discussed herein, the embodiments of the present invention relate to systems and methods for obtaining health and financial information with a handheld device. More particularly, the present invention relates to utilizing a bar-code reader or RF ID reader on a handheld device to obtain real time health and financial information. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed and desired to be secured by Letters Patent is:

1. A method for obtaining financial information about a product prior to purchase comprising the acts of:
   using a computing device, scanning a product bar code and obtaining a product identity;
   using the computing device, obtaining a product price corresponding to the product identity;
   using the computing device, recording the product price and product identity;
   using the computing device, assigning the recorded product price and the recorded product identity to a particular financial category;

using the computing device, displaying a financial record over a particular time period including the recorded product price and product identity; and wherein the acts are performed in the order listed above.

2. The method of claim 1 further includes matching the product identity with other product information including one of alternative retailer price, alternative brand price, available coupons, generic price, product reviews, and value rating.

3. The method of claim 1, wherein the act of obtaining a product price corresponding to the product identity includes digitally capturing and textually recognizing the advertised price on the store display.

4. The method of claim 1, wherein the act of obtaining a product price corresponding to the product identity includes downloading a particular store's price list and correlating the product identity with the corresponding product price.

5. The method of claim 1 further includes displaying current financial budget information including the product price.

6. The method of claim 1, wherein the act of scanning a product bar code and obtaining product price and product identity further includes disposing a bar code reader on a handheld device in close proximity to the product bar code.

7. The method of claim 1, wherein the act of scanning a product bar code and obtaining a product identity includes receiving a RF ID code.

8. A handheld computing device comprising:
a scanning device configured to obtain a product identity from a bar code;
a correlation module that is configured to correlate the product identity obtained by the scanning device with information about the product wherein the information includes financial information;
wherein the correlation module is configured to assign the product identity obtained by the scanning device and the information about the product correlated by the correlation module to a particular category;
a memory module configured to store the information about the product correlated by the correlation module; and
a display that is configured to visually display the information about the product stored by the memory module.

9. The handheld device of claim 8, wherein the correlation module further includes a data communication system.

10. The handheld device of claim 8, wherein the scanning device is configured to receive radio frequency transmissions.

* * * * *

(12) INTER PARTES REEXAMINATION CERTIFICATE (790th)
United States Patent
Baker

(10) Number: US 7,917,401 C1
(45) Certificate Issued: Jan. 9, 2014

(54) SYSTEMS AND METHODS FOR OBTAINING HEALTH AND FINANCIAL INFORMATION WITH A HANDHELD DEVICE

(75) Inventor: Trent Baker, Salt Lake City, UT (US)

(73) Assignee: Epic Technology, Salt Lake City, UT (US)

Reexamination Request:
No. 95/002,026, Jun. 20, 2012

Reexamination Certificate for:
Patent No.: 7,917,401
Issued: Mar. 29, 2011
Appl. No.: 11/277,994
Filed: Mar. 30, 2006

Related U.S. Application Data

(60) Provisional application No. 60/667,933, filed on Apr. 4, 2005.

(51) Int. Cl.
*G06Q 30/00* (2012.01)

(52) U.S. Cl.
USPC ............. 705/26.1; 705/27.1; 705/30; 186/61; 715/744; 715/766

(58) Field of Classification Search
None
See application file for complete search history.

(56) References Cited

To view the complete listing of prior art documents cited during the proceeding for Reexamination Control Number 95/002,026, please refer to the USPTO's public Patent Application Information Retrieval (PAIR) system under the Display References tab.

*Primary Examiner* — Anjan Deb

(57) ABSTRACT

The present invention relates to systems and methods for obtaining financial information with a handheld device. One embodiment of the present invention relates to a system for obtaining real time financial information utilizing a bar code or RF ID reader on a handheld device. A bar code or RF ID reader is used to obtain the product identity of a particular product in a retail environment. The product identity is correlated with the particular retailer's product price. This information can then be analyzed versus current financial budgets or recorded as part of a financial plan. In addition, real time financial advice and information can be given on the product including whether a competitor offers a lower price on a similar product, consumer reviews of the product, value rating, etc. The bar code or RF ID reader may be incorporated into any existing handheld device including a PDA, media player, cell phone, calculator, watch, or shopping device.

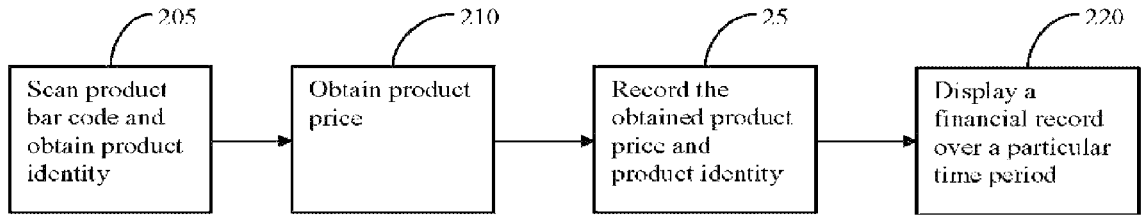

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-10 are cancelled.

\* \* \* \* \*